US008557254B2

(12) United States Patent
Biermann et al.

(10) Patent No.: US 8,557,254 B2
(45) Date of Patent: Oct. 15, 2013

(54) *LAWSONIA INTRACELLULARIS* BACTERIUM OF A NOVEL SEROTYPE, VACCINE BASED ON THAT BACTERIUM, ANTIBODIES SUITABLE FOR DIAGNOSING THE NOVEL *LAWSONIA INTRACELLULARIS* SEROTYPE AND HYBRIDOMAS FOR PRODUCING THE SAID ANTIBODIES

(75) Inventors: Yvonne Maria Johanna Corina Biermann, Boxmeer (NL); Mohamad Morsey, Elkhorn, NE (US); Antonius Arnoldus Christiaan Jacobs, Boxmeer (NL); Carla Christina Schrier, Boxmeer (NL)

(73) Assignees: Intervet Inc., Summit, NJ (US); Intervet International B.V., Boxmeer (NL)

( * ) Notice: Subject to any disclaimer, the term of this patent is extended or adjusted under 35 U.S.C. 154(b) by 183 days.

(21) Appl. No.: 13/054,979

(22) PCT Filed: Jul. 20, 2009

(86) PCT No.: PCT/EP2009/059279
§ 371 (c)(1),
(2), (4) Date: Jan. 20, 2011

(87) PCT Pub. No.: WO2010/010055
PCT Pub. Date: Jan. 28, 2010

(65) Prior Publication Data
US 2011/0129500 A1   Jun. 2, 2011

Related U.S. Application Data

(60) Provisional application No. 61/082,552, filed on Jul. 22, 2008.

(30) Foreign Application Priority Data

Aug. 13, 2008   (EP) .................................... 08162299

(51) Int. Cl.
*A61K 39/02*   (2006.01)

(52) U.S. Cl.
USPC ................... 424/234.1; 424/190.1; 424/184.1

(58) Field of Classification Search
None
See application file for complete search history.

(56) References Cited

U.S. PATENT DOCUMENTS 7,022,328 B1 * 4/2006 Panaccio et al. ........... 424/234.1
7,312,065 B2 * 12/2007 Roof et al. ................. 435/252.1

(Continued)

FOREIGN PATENT DOCUMENTS

EP   0843818   6/1995
EP   1219711   * 6/2006

(Continued)

OTHER PUBLICATIONS van der Heijden, Hmjf et al, Research in Veterinary Science, vol. 77, pp. 197-202, 2004, Prevalence of exposure and infection of *Lawsonia intracellularis* among slaughter-age pigs.*

(Continued)

Primary Examiner — Albert Navarro
Assistant Examiner — Ginny Portner
(74) Attorney, Agent, or Firm — William M. Blackstone

(57) ABSTRACT

This invention pertains to *Lawsonia intracellularis* bacterium of a serotype which is reactive with monoclonal antibody INT-LIC-02-02 as produced by hybridoma INT-LIC-02-02 deposited with the Collection Nationale de Cultures de Micro-organismes of the Institut Pasteur at Paris France under nr. CNCM I-4049 but which is not reactive with antibody INT-LIC-01-28 as produced by hybridoma INT-LIC-01-28 deposited with the Collection Nationale de Cultures de Micro-organismes of the Institut Pasteur at Paris France under nr. CNCM I-4048. The invention also pertains to vaccines for protection against an infection with *Lawsonia intracellularis* based on those novel bacteria, antibodies suitable for diagnosing the novel *Lawsonia intracellularis* serotype and hybridomas for producing the said antibodies.

8 Claims, 2 Drawing Sheets

(56) References Cited

U.S. PATENT DOCUMENTS

Figure 1:
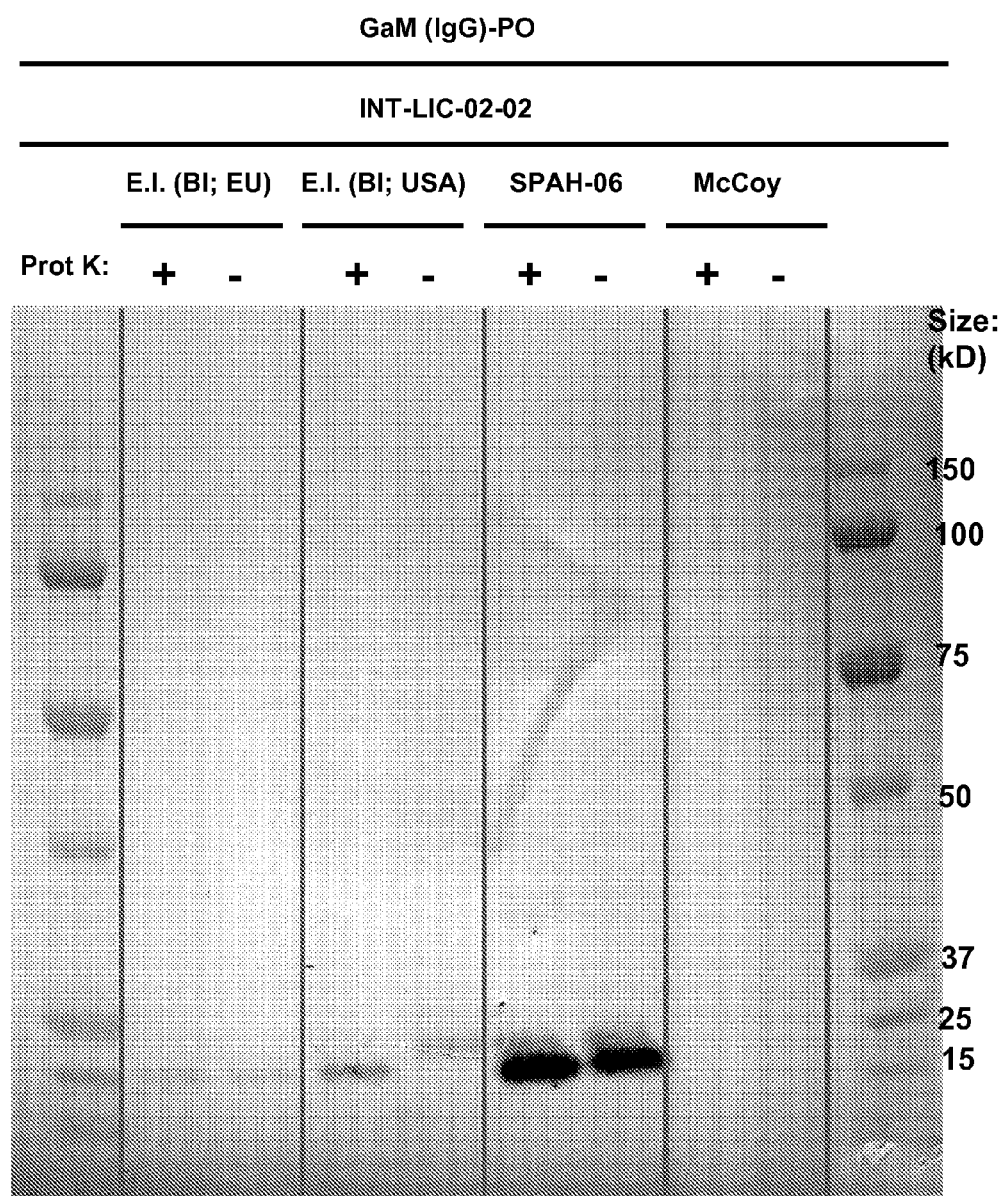

| | | | |
|---|---|---|---|
| 7,550,270 B2* | 6/2009 | Kroll et al. | 435/7.32 |
| 2005/0069559 A1* | 3/2005 | Jacobs et al. | 424/190.1 |
| 2005/0250150 A1* | 11/2005 | Jacobs et al. | 435/6 |
| 2006/0035287 A1* | 2/2006 | Kroll et al. | 435/7.2 |
| 2007/0212373 A1* | 9/2007 | Vermeij | 424/200.1 |

FOREIGN PATENT DOCUMENTS

| | | |
|---|---|---|
| WO | WO 96/39629 | 12/1996 |
| WO | WO 97/20050 | 6/1997 |
| WO | WO 2005/011731 | 2/2005 |
| WO | WO 2005/070958 | 8/2005 |
| WO | WO 2006/012949 | 2/2006 |
| WO | 2009/127684 * | 10/2009 |

OTHER PUBLICATIONS

Dauvillier, J et al, Canadian Veterinary Journal, 2006, vol. 47, pp. 689-691, Diagnostic and epidemiological features of *Lawsonia intracellularis* enteropathy in 2 foals.*

Boesen, Henrietta T et al, Veterinary Microbiology, vol. 105, 2005, pp. 199-206, Development, characterization and diagnostic application of a monoclonal antibody specific for a proteinase K resistant *Lawsonia intracellularis* antigen.*

Roof, MB, PhD, Vaccinatin for ileitis, Boehringer Ingelheim Vetmedica, Inc, Ames, Iowa, 2001 Allen D. Leman Swine Conference, pp. 121-126.*

Boesen et al, "Development, Characterization and Diagnostic Application of a Monoclonal Antibody Specific for a Proteinase K Resistant *Lawsonia intracellularis* Antigen", Veterinary Microbiology, vol. 105, No. 3-4, pp. 199-206 (2005).

Gebhart et al, "Ileal Symbiont Intracellularis, An Obligate Intracellular Bacterium of Porcine Intestines Showing a Relationship to Desulfovibrio Species", International Journal of Systemic Bacteriology, vol. 43, No. 3, pp. 533-538 (1993).

Guedes et al, "Comparison of Intestinal Mucosa Homogenate and Pure Culture of the Homologous *Lawsonia intracellularis* Isolate in Reproducing Proliferative Enteropathy in Swine", Veterinary Microbiology, vol. 93, pp. 159-166 (2003).

Lawson et al, "Intracellular Bacteria of Porcine Proliferative Enteropathy: Cultivation and Maintenance in Vitro", Journal of Clinical Microbiology, vol. 31, No. 5, pp. 1136-1142 (1993).

Kroll et al, "Lipopolysaccharide-Based Enzyme-Linked Immunosorbent Assay for Experimental Use in Detection of Antibodies to *Lawsonia intracellularis* in Pigs", Clinical and Diagnostic Laboratory Immunology, American Society for Microbiology, vol. 12, No. 6, pp. 693-699 (2005).

Kroll et al, "Proliferative Enteropathy: A Global Enteric Disease of Pigs Caused by *Lawsonia Intracellularis*", Animal Health Research Reviews, vol. 6, No. 2, pp. 173-197 (2005) [Abstract].

McOrist et al, "Characterization of *Lawsonia intracellularis* Gen. Nov., SP. Nov., The Obligately Intracellular Bacterium of Porcine Proliferative Enteropathy", International Journal of Systematic Bacteriology, Society for General Microbiology, vol. 45, No. 4, pp. 820-825 (1995).

Towbin et al, "Electrophoretic Transfer of Proteins from Polyacrylamide Gels to Nitrocellulose Sheets: Procedure and Some Applications", Proceedings of the National Academy of Sciences of the United States of America, vol. 76, pp. 4350-4354 (1979).

International Search Report in corresponding PCT/EP2009/059279, mailed Nov. 16, 2009.

* cited by examiner

LAWSONIA INTRACELLULARIS BACTERIUM OF A NOVEL SEROTYPE, VACCINE BASED ON THAT BACTERIUM, ANTIBODIES SUITABLE FOR DIAGNOSING THE NOVEL LAWSONIA INTRACELLULARIS SEROTYPE AND HYBRIDOMAS FOR PRODUCING THE SAID ANTIBODIES

RELATED APPLICATIONS

This application is a national stage entry under 35 U.S.C. §371 of PCT/EP2009/059279 filed on Jul. 20, 2009, which claims priority to EP Application No. 08162299.5 filed on Aug. 13, 2008 and U.S. Provisional Application No. 61/082,552 filed on Jul. 22, 2008.

The present invention pertains to *Lawsonia intracellularis* bacteria of a novel serotype, vaccines for protection against an infection with *Lawsonia intracellularis* based on those novel bacteria, antibodies suitable for diagnosing the novel *Lawsonia intracellularis* serotype and hybridomas for producing the said antibodies.

Proliferative enteropathy (PE, also called enteritis or ileitis) in virtually all animals (humans, rabbits, horses, dogs, foxes, ostriches, ferrets, guinea pigs, etc.), in particular pigs, presents a clinical sign and pathological syndrome with mucosal hyperplasia of immature crypt epithelial cells, primarily in the terminal ileum. Other sites of the intestines that can be affected include the jejunum, caecum and colon. Weanling and young adult pigs are principally affected with typical clinical manifestation of rapid weight loss and dehydration. Natural clinical disease in pigs occurs worldwide. The disease is consistently associated with the presence of intracellular curved bacteria, presently known as *Lawsonia intracellularis*. These bacteria have been identified in 1993 as a novel taxonomic genus and species, originally referred to as Ileal symbiont intracellularis (International Journal of Systemic Bacteriology, Vol. 43, No. 3, 533-538, 1993; Gebhart et al.). It is an obligate intracellular, curved, gram-negative bacterium as described by Gebhart in the reference identified here-above and by McOrist in the same Journal, Vol. 45, No. 4, 820-825, 1995). Since 1995 the bacteria are generally referred to as *Lawsonia intracellularis*.

In general, vaccination against *Lawsonia intracellularis* has shown to be an economically efficient measure to control Ileitis and to allow a good exploitation of the genetic growth potential of the pig (Porcine Proliferative Enteropathy Technical manual 3.0, July 2006; available from Boehringer Ingelheim).

Recently, it was found that a dominant antigen is a carbohydrate of *Lawsonia intracellularis* cells, which carbohydrate is in association with the outer cell membrane of these cells (see patent applications EP 08154764.8 and U.S. 61/046,161 filed 18 Apr. 2008 and assigned to Intervet International B.V.). It has appeared that a vaccine which is based on a composition containing the isolated carbohydrate is able to provide adequate protection against an infection with *Lawsonia intracellularis* when compared with existing vaccines. Indeed, monoclonal antibodies derived against antigenic determinants of this carbohydrate are reactive with all publicly available strains, such as the strains used in the commercially available live vaccines ENTERISOL®ILEITIS in Europe and the USA (which strains are referred to as BI; EU and BI; USA respectively in the remainder of this document).

It has now surprisingly been found that *Lawsonia intracellularis* bacteria of a new serotype exist, which bacteria in particular with regard to the dominant carbohydrate antigen differ substantially from bacteria of a known serotype. This new serotype has been shown to be present in pigs in the USA and in pigs and horses in the Netherlands. A bacterium of the new serotype is characterised in that is reactive with monoclonal antibody INT-LIC-02-02 as produced by hybridoma INT-LIC-02-02 deposited under the Budapest Treaty on Oct. 27, 2008, with the Collection Nationale de Cultures de Microorganismes of the Institut Pasteur, 25, Rue du Docteur Roux, Paris, France under nr. CNCM I-4049, but not reactive with antibody INT-LIC-01-28 as produced by hybridoma INT-LIC-01-28 deposited under the Budapest Treaty on Oct. 27, 2008, with the Collection Nationale de Cultures de Microorganismes of the Institut Pasteur, 25, Rue du Docteur Roux, Paris, France under nr. CNCM I-4048. Both these monoclonals are directed against antigenic determinants of the dominant carbohydrate antigen of the known *Lawsonia intracellularis* serotype.

The bacterium according to the invention may be in any form, for example a live wild-type form, a live mutant form, in particular a live attenuated form such as known from EP 0 843 818, which mutant may also be a recombinant one, or killed, such as known from the above mentioned patent applications filed on 18 Apr., 2008.

Whether or not a *Lawsonia intracellularis* bacterium is reactive with the monoclonals as described here-above can be tested in an immunoblotting procedure as described in the appended examples in the paragraph "Immunocharacterisation of bacteria and tissue slides") with respect to isolated bacteria.

Since the new serotype immunologically differs from the existing one, diagnosing the new serotype requires the use of a new set of antibodies. Moreover, since the new serotype is immunologically different in particular with regard to the dominant antigen, it is reasonably expected that existing vaccines based on the known serotype will provide less adequate protection, or even do not provide protection at all against an infection with *Lawsonia intracellularis* of the new serotype. The current invention also encompasses vaccines based on *Lawsonia intracellularis* bacteria of the new serotype.

In an embodiment the *Lawsonia intracellularis* bacterium is derived from a strain as deposited with the Collection Nationale de Cultures de Micro-organismes of the Institut Pasteur at Paris France under nr. CNCM I-4050. In this embodiment, "a strain as deposited" means a strain that has the characteristics of the strain as deposited. A derivative may for example be a live attenuated one, for example produced by passing the bacterium a sufficient number of times such as known for example from EP 0 843 818, or produced by recombinant techniques. It may also be a killed bacterium, such as for example known from European patent application EP 08154764.8. In a further embodiment, the *Lawsonia intracellularis* bacterium is the strain deposited with the Collection Nationale de Cultures de Micro-organismes of the Institut Pasteur at Paris France under nr. CNCM I-4050. This strain has emerged in the USA and it is believed that a vaccine comprising antigens from this strain will provide optimal protection against this strain or other strains of the same serotype.

In an embodiment, the invention pertains to an isolated fraction derived from a bacterium according to any of the preceding claims. Such an isolated derived fraction may be a component or mixture of components isolated of the bacterium itself or, if applicable, a metabolite of that bacterium, or a subunit of the bacterium which is e.g. expressed by a recombinant producing micro-organism that expresses the subunit. An isolated fraction can be useful in the development of a diagnostic kit for assessing infection with *Lawsonia intracellularis* bacteria of the new serotype. Also, in particular when the isolated fraction comprises relevant antigens for providing protection against an infection with *Lawsonia intracellularis*, it may be successfully used in a safe vaccine against such infection. An isolated fraction of the bacterium, when administered to an animal, typically will not cause the same disease or disorder as the wild-type bacterium, or at least to a lesser extent.

In an embodiment the isolated fraction comprises a non-live carbohydrate containing composition, the carbohydrate being also found in live *Lawsonia intracellularis* cells in association with the outer cell membrane of these cells. How to obtain such a fraction of *Lawsonia intracellularis* is described for example in "Example 1" of the European patent application EP 08154764.8. This is also known from Kroll et al. (Clinical and Diagnostic Laboratory Immunology, June 2005, 693-699).

The present invention also pertains to a vaccine for protection against an infection with *Lawsonia intracellularis*, wherein the vaccine comprises a bacterium of the novel serotype and/or an isolated fraction of such a bacterium. A vaccine for protection against an infection with microorganisms in the sense of this invention is a constitution suitable for application to an animal, comprising one or more antigens such as attenuated or killed microorganisms and/or subunits thereof, or any other substance such as a metabolite of an organism, in an immunologically effective amount, i.e. capable of stimulating the immune system of the target animal sufficiently, to at least reduce the negative effects of a challenge of the wild-type micro-organisms, typically combined with a pharmaceutically acceptable carrier such as a liquid containing water, optionally comprising immunostimulating agents (adjuvants), which upon administration to the animal induces an immune response for aiding in preventing, ameliorating or treating a disease or disorder.

In general, a vaccine can be manufactured by using art-known methods that basically comprise admixing the antigens (or a composition containing the antigens) with a pharmaceutically acceptable carrier, e.g. a liquid carrier such as (optionally buffered) water or a solid carrier such as commonly used to obtain freeze-dried vaccines. In the vaccine, the antigens are present in an immunologically effective amount, i.e. in an amount capable of stimulating the immune system of the target animal sufficiently to at least reduce the negative effects of a post-vaccination challenge of the wild-type micro-organisms. Optionally other substances such as adjuvants, stabilisers, viscosity modifiers or other components are added depending on the intended use or required properties of the vaccine. In principal, each substance that is able to favor or amplify a particular process in the cascade of immunological events, ultimately leading to a better immunological response (i.e. the integrated bodily response to an antigen, in particular one mediated by lymphocytes and typically involving recognition of antigens by specific antibodies or previously sensitized lymphocytes), can be defined as an adjuvant. Note that the adjuvant is in general not required for the said particular process to occur, but favors or amplifies the said process. For parenteral vaccination many forms are suitable, in particular liquid formulations (with dissolved, emulsified or suspended antigens) but also solid formulations such as implants or an intermediate form such as a solid carrier for the antigen suspended in a liquid. Parenteral vaccination and suitable (physical) forms of vaccines for parenteral vaccination have been known for more than 200 years.

In a further embodiment the vaccine contains non-live *Lawsonia intracellularis* antigens and is in a form suitable for systemic administration at an antigenic dose per vaccination derived from or containing at least $1\times10^7$ (1 E7) *Lawsonia intracellularis* cells. We have shown that by applying a dose per vaccination derived from or containing at least $1\times10^8$ (1 E8) *Lawsonia intracellularis* cells), still an good protection can be arrived at. Based on these results, it is believed that a dose of $1\times10^7$ is the minimum required amount for adequate protection when non-live antigen is given systemically. In principal there is no upper limit in the dose. However, at a dose typically higher than $1\times10^{11}$ cells/ml a vaccine will be difficult to administer systemically due to its high load of antigenic mass. For subunits, a practical upper limit typically is an antigenic mass per ml derived from or corresponding to $1\times10^{14}$ cells. Systemic administration is a form of administration wherein the vaccine reaches the circulatory system of the body (comprising the cardiovascular and lymphatic system), thus affecting the body as a whole rather than a specific locus such as the gastro-intestinal tract. Systemic administration can be performed e.g. by administering the antigens into muscle tissue (intramuscular), into the dermis (intradermal), underneath the skin (subcutaneous), underneath the mucosa (submucosal), in the veins (intravenous) etc. Apart from the very good protection obtainable, an important advantage of a non-live vaccine is that it is an inherent safety when compared to a live vaccine. The dose of this embodiment appears to be a minimum value to obtain acceptable protection with this form of administration.

The invention also pertains to antibodies suitable for diagnosing the novel *Lawsonia intracelluaris* serotype, in particular the antibodies that belong to the group as produced by hybridoma INT-LIC-02-02 or hybridoma INT-LIC-01-28, both deposited with the Collection Nationale de Cultures de Micro-organismes of the Institut Pasteur at Paris France under nr. CNCM I-4049 and CNCM I-4048 respectively. The invention also pertains to these hybridomas.

The invention will be further explained based on the following examples of embodiments of the present invention Isolation of *Lawsonia intracellularis* from Intestines Tissue material was obtained from the intestines of pigs born and grown in the USA, which pigs had naturally occurring cases of histologically confirmed proliferative enteropathy. *Lawsonia intracellularis* bacteria were harvested using commonly known techniques, known inter alia from Lawson et al. (Journal of Clinical Microbiology, May 1993, p. 1136-1142) under "MATERIALS AND METHODS", paragraph "Source material". The *Lawsonia intracellularis* bacteria were grown in a mouse fibroblast (McCoy's) cell line in T-175 cm$^2$ flasks using methods established in the art (Guedes and Gebhart, Veterinary Microbiology, 93:159-166. 2003). Bacteria were harvested form tissue culture supernatants and from infected McCoy cells as described in the art (Guedes and Gebhart, Veterinary Microbiology, 93:159-166. 2003). These bacteria, referred to in this application as *Lawsonia intracellularis* isolate SPAH06, and deposited with the Collection Nationale de Cultures de Micro-organismes of the Institut Pasteur at Paris France under nr. CNCM I-4050, were used for characterising the new serotype as well as for preparation of a vaccine.

Tissue Samples from Animals in the Netherlands

Tissue material was obtained from the intestines of a horse and a pig grown in the Netherlands, which animals were suspected of having proliferative enteropathy caused by *Lawsonia intracellularis*. The horse was a 5-month-old Friesian foal with severe hypoproteinaemia and thickened gutwall as determined by ultrasound scan. It was submitted to a veterinary clinic. Because of the clinical signs it was suspected for having an infection with *Lawsonia intracellularis*. The pig was also suspected of having an infection with *Lawsonia intracellularis*. In order to confirm this, tissue samples from the intestines of these animals were collected, fixed in neutral buffered formalin and processed into slides according to standard procedures. These slides were examined microscopically and subjected to immunohistochemistry. The microscopic examination confirmed that Lawsonia (like) bacteria were present. Here-beneath, the results with respect to the immunohistochemistry are described.

Production of Monoclonals and Hybridomas

Monoclonal antibodies (also referred to as monoclonals) were produced as follows. Lawsonia intracellularis bacteria were isolated from infected pig gut tissue essentially as described by Lawson et al (1993) referred to here-above. The isolated bacteria were further purified by percol gradient centrifugation. From the purified cells outer membrane preparations were made by sonification followed by N-Lauroyl Sarcosine extraction. The outer membrane preparations were formulated in a paraffin based water-in-oil emulsion and administered two times intramuscularly to Balb/c mice (with a 6-weeks interval). One week after an additional intravenous booster vaccination, hybridomas were produced by fusing spleen cells (B-lymphocytes) of the vaccinated mice with mouse myeloma cells (NS-1) by using a standard Poly-Ethylene-glycol (PEG) fusion method. The hybridomas were cultured for about two weeks in Hypoxanthine-Aminopterin-Thymidine (HAT) selection medium and screened with a specific ELISA and/or Immunofluorescence (IF) test. Positive clones were picked and stored in liquid nitrogen. The monoclonals are referred to as INT-LIC-01-028 and INT-LIC-02-02. In line with Example 1 of patent application EP 08154764.8 it was established that the monoclonals were both reactive with an outer membrane associated carbohydrate of Lawsonia intracellularis bacteria.

Immunocharacterisation of Bacteria and Tissue Slides

Immunocharacterisation of isolated Lawsonia bacteria was carried using standard blotting techniques, viz. SDS-PAGE using a NuPage 10% Bis-Tris gel under reducing conditions with a MOPS/MES SDS buffer. The semi-dry Western blotting method according to Towbin (Towbin, H; Staehlin, T. and Gordon, J. Proc. Nat. Acad. Sci. 76, 4350, 1979) was used to blot the gel onto a Immobilon P transfer membrane PVDF 0.45 um (Millipore). The blot was blocked with 100 ml 0.04 M PBS containing 0.5% Tween 20 (pH=7.2) and 1% m/v milkpowder for one hour at 37° C. The blot was washed once with 0.04 M PBS and 0.5% Tween 20 (pH=7.2) for 30 seconds. Subsequently, the blot was incubated for one hour at 37° C. in 20 ml 0.04 M PBS containing 0.05% Tween 20 and 1% milkpowder containing a 200 times dilution of one of the monoclonal antibodies, followed by washing three times for five minutes with 100 ml 0.04 M PBS containing 0.5% Tween 20 (pH=7.2). Then the blot was incubated for one hour at 37° C. with 20 ml 0.04 M PBS containing 0.05% Tween 20 and 1% milkpowder and 1000 times diluted Goat-anti-Mouse (IgG)-HRP, followed by washing three times for five minutes with 100 ml 0.04 M PBS containing 0.5% Tween 20 (pH=7.2). The blot was incubated in substrate Vector SG solution (Vector SG substrate kit for peroxidase (Vector, SK-4700)) until there was sufficient color development. The reaction was stopped by washing two times for five minutes in WFI (water for injection).

Figure 2:
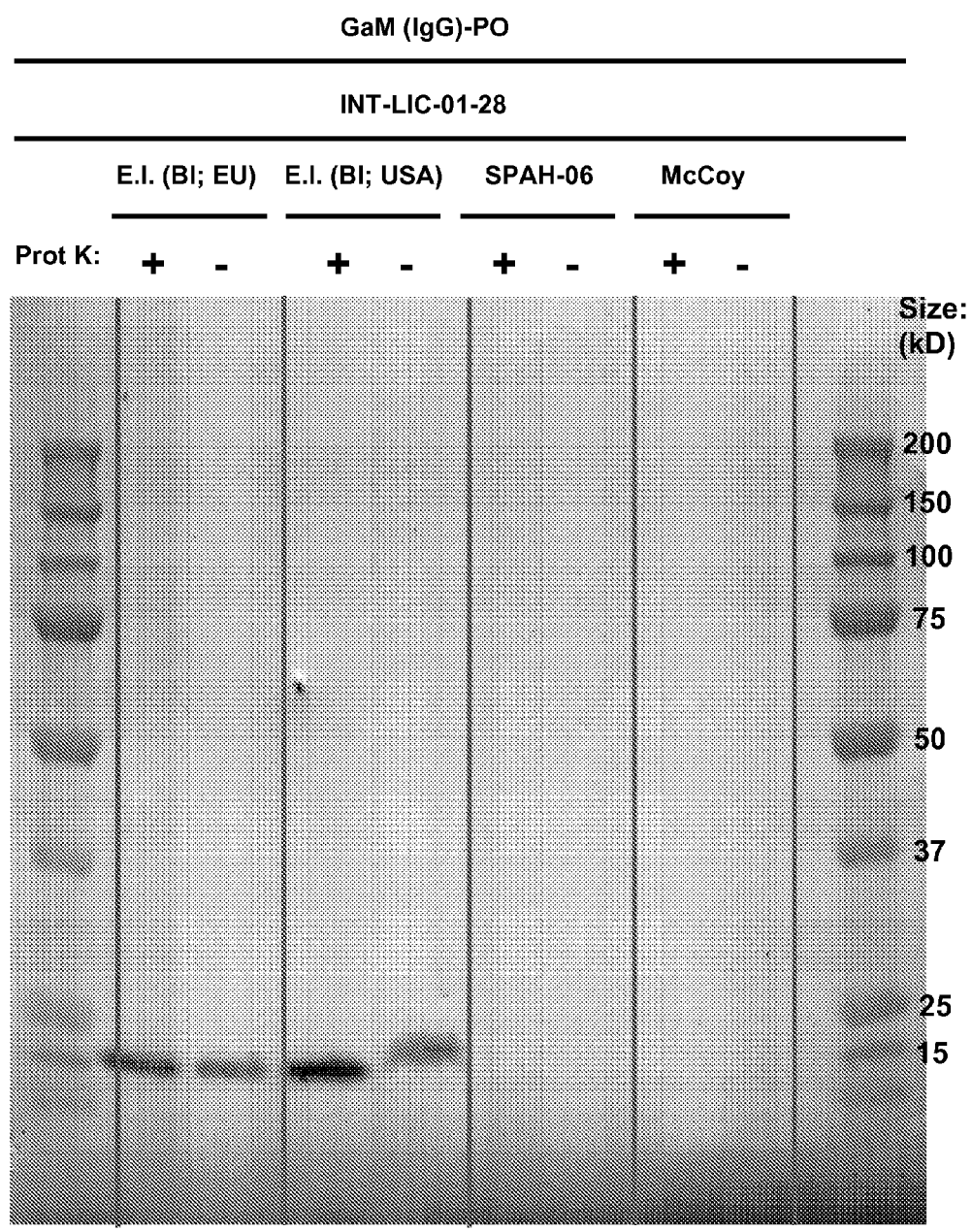

The results are depicted in FIGS. 1 and 2. FIG. 1 shows the staining results using monoclonal antibody INT-LIC-02-02. It is clear that this monoclonal reacts with the publicly known strains BI; EU and BI; USA with a band of about 15 kDa. It can also be seen that these two strains differ slightly since the preparations not treated with proteinase K (indicated as Prot K:-) differ slightly in molecular weight. There is also a positive reaction with strain SPAH06. The control (McCoy cell preparation) gives no staining. In FIG. 2 the staining results are given with monoclonal antibody INT-LIC-01-028. This monoclonal seems to react with the same carbohydrate antigen of the strains BI; EU and BI; USA. However, under these circumstances there is no reaction between monoclonal INT-LIC-01-028 and a preparation of strain SPAH06 in the sense of the present invention since there is no visible band found in this procedure. It is noted that some slight a-specific reaction with monoclonal INT-LIC-01-28 might occur with Lawsonia intracellularis bacteria of the novel serotype, but under the circumstances as described here-above, such an a-specific reaction could not be detected using the prescribed visualization technique (i.e. stopping with the Vector VG incubation until sufficient color development is produced for the two BI strains).

Immunocharacterisation of tissues samples of Lawsonia infected gut was carried out as follows. Tissue samples were fixed in neutral buffered formalin and processed into slides according to standard procedures. Lawsonia bacteria present in the tissue slides were probed with monoclonal INT-LIC-01-28 or INT-LIC-02-02 and then visualized by using Mouse-EnVision™ System/HRP (available from DAKO, Carpinteria, Calif., USA). Tissues samples from the Dutch horse and pig as mentioned here-above in the paragraph "Tissue samples from animals in The Netherlands" were subjected to this immunocharacterisation test. When monoclonal INT-LIC-02-02 was used to probe the tissue slides specific staining could be observed whereas monoclonal INT-LIC-01-28 did not result in specific positive staining.

From these cases it can be concluded that several Lawsonia intracellularis strains of the novel immunological serotype as defined in the introductory part of this description here-above and the appended claims, are present in different animal species. Each of these strains is associated with clinical signs and tissue lesions corresponding to proliferative enteropathy.

Vaccination Studies with Lawsonia intracellularis Isolate SPAH06

A study was conducted in pigs to test whether a killed vaccine based on Lawsonia intracellularis isolate SPAH06 could provide protection against the disease caused by Lawsonia. The live bacteria were inactivated by addition of Binary Ethyleneimine (BEI) and then formulated in the Emunade® adjuvant (available from Intervet Schering-Plough Animal Health). The inactivated and adjuvanted bacteria were tested at two dose levels; $1 \times 10^8$ and $5 \times 10^8$ bacteria per dose. Challenge with a gut homogenate prepared from the intestine of a pig diagnosed with Lawsonia infection took place on day 42. The primary measure of efficacy was based on significant ($p<0.05$) reduction in prevalence and severity of macroscopic and microscopic lesions in the ileum of vaccinated versus control animals. The macroscopic lesions were scored based on a scale of 0-3 and microscopic lesions were scored based on a scale of 0-4. The study schedule and major activities are shown in Table 1. The results of this study are shown in Table 2. The data presented in Table 2 show that there was a significant reduction in ileum lesions scores between vaccinated animals and placebo control (t-test, $p<0.05$). Furthermore, there was a significant reduction in the colonization of vaccinated animals versus placebo control as determined by immunohistochemical staining of affected ileal tissues. These data demonstrate that vaccination of pigs with a bacterin based on inactivated Lawsonia intracellularis isolate SPAH06 results in significant protection against the disease caused by this type of bacterium.

TABLE 1

Treatment groups and vaccination/challenge activities

| Treatment Group | No. of Animals | Vaccine dose | Dose/ Route | Vaccination (Study Day) | Serum Collection Days | Nec-ropsy Days |
|---|---|---|---|---|---|---|
| A | 15 | $5 \times 10^8$ | 2 ml/IM | 0, 21 | 0, 21, 42, 63 | 63 |
| B | 15 | $1 \times 10^8$ | 2 ml/IM | 0, 21 | 0, 21, 42, 63 | 63 |
| C | 15 | — | 2 ml/IM | 0, 21 | 0, 21, 42, 63 | 63 |

TABLE 2

Impact of vaccination with *Lawsonia bacterin* on crypt epithelium colonization and Ileal lesions

| Treatment | Ileum lesion score | IHC score | % animals positive for *Lawsonia* |
|---|---|---|---|
| $5 \times 10^8$ | 0.33 ± 0.15 | 1.1 ± 0.31 | 54 |
| $1 \times 10^8$ | 0.36 ± 0.14 | 1.56 ± 0.25 | 91 |
| Control | 1.0 ± 0.19 | 2.53 ± 0.18 | 100 |

The invention claimed is:

1. A isolated and characterized *Lawsonia intracellularis* bacterium having an outer cell membrane antigen that is reactive with monoclonal antibody INT-LIC-02-02 as produced by hybridoma INT-LIC-02-02 deposited with the Collection Nationale de Cultures de Micro-organismes of the Institut Pasteur at Paris, France under nr. CNCM I-4049 but not reactive with antibody INT-LIC-01-28 as produced by hybridoma INT-LIC-01-28 deposited with the Collection Nationale de Cultures de Micro-organismes of the Institut Pasteur at Paris, France under nr. CNCM I-4048.

2. The *Lawsonia intracellularis* bacterium according to claim 1 derived from a strain as deposited with the Collection Nationale de Cultures de Micro-organismes of the Institut Pasteur at Paris, France under nr. CNCM I-4050.

3. The *Lawsonia intracellularis* bacterium according to claim 1, wherein the bacterium is deposited with the Collection Nationale de Cultures de Micro-organismes of the Institut Pasteur at Paris France under nr. CNCM 1-4050.

4. A vaccine for protecting an animal against an infection with *Lawsonia intracellularis*, comprising an immunogenically effective amount of a bacterium according to claim 1 and a pharmaceutically acceptable carrier.

5. The vaccine according to claim 4, comprising an immunogenically effective amount of non-live *Lawsonia intracellularis* in a form suitable for systemic administration, in a dose per vaccination of at least $1 \times 10^7$ *Lawsonia intracellularis* cells.

6. The vaccine according to claim 4, wherein the bacterium is inactivated.

7. The vaccine according to claim 4, wherein the bacterium is a strain as deposited with the Collection Nationale de Cultures de Microorganismes of the Institute Pasteur at Paris, France under nr. CNCM I-4050.

8. A composition comprising an isolated *Lawsonia intracellularis* carbohydrate outer cell membrane antigen, said antigen being reactive with monoclonal antibody INT-LIC-02-02 as produced by hybridoma INT-LIC-02-02 deposited with the Collection Nationale de Cultures de Micro-organismes of the Institut Pasteur at Paris, France under nr. CNCM 1-4049 but not reactive with antibody INT-LIC-01-28 as produced by hybridoma INT-LIC-01-28 deposited with the Collection Nationale de Cultures de Micro-organismes of the Institut Pasteur at Paris, France under nr. CNCM 1-4048.

* * * * *